United States Patent [19]

Metsada

[11] Patent Number: 5,384,123
[45] Date of Patent: Jan. 24, 1995

[54] TOPICAL COMPOSITION AND METHOD FOR REJUVENATING SKIN

[76] Inventor: Albert Metsada, 3 Gordon Street, Kiryat Hayovel, Jerusalem, Israel

[21] Appl. No.: 86,863

[22] Filed: Jul. 7, 1993

[30] Foreign Application Priority Data

Sep. 8, 1992 [IL] Israel ............................. 103101

[51] Int. Cl.⁶ ............ A61K 35/78; C07G 17/00
[52] U.S. Cl. ..................... 424/195.1; 424/74; 514/929
[58] Field of Search ............ 424/195.1, 74; 514/929

[56] References Cited

U.S. PATENT DOCUMENTS 4,520,012  5/1985  Alfonsi .................. 424/549
5,069,898  12/1991  Goldberg .............. 424/70

OTHER PUBLICATIONS

Hertz, Chem Abs. 96:223321p, 1982.
Berdel Chem Abs. 107:205183m 1987.
Hatano Chem Abs 116:113579c, 1992.
Sticher et al., Chem Abs. 116:1105uk, 1992.

*Primary Examiner*—John W. Rollins
*Assistant Examiner*—Howard C. Lee
*Attorney, Agent, or Firm*—Larson & Taylor

[57] ABSTRACT

The invention provides a topical composition for rejuvenating skin texture, comprising a first topically applicable component for stimulating the flow of blood in the arteries leading to, and capillaries feeding the muscles adjacent the skin; and a second topically applicable component for stimulating the flow of blood in the capillaries adjacent skin cells.

14 Claims, No Drawings

TOPICAL COMPOSITION AND METHOD FOR REJUVENATING SKIN

The present invention relates to a topical composition and method for rejuvenating skin and skin texture.

More particularly, the present invention relates to a topical composition for rejuvenating skin and skin texture, which composition incorporates natural beneficial herbs and condiment plants which have previously been used for other purposes.

Almost as far back as the beginning of recorded history, mankind in general and women in particular have searched for means to maintain the youthful appearance of their skin and to rejuvenate the same. Thus, e.g., there are the stories of Cleopatra taking milk baths in accordance with the ancient belief of the association of youthfulness with milk, and of the use of aromatic oil blends by high court personalities for treatment of the entire body.

In more recent times, the cosmetic industry has engaged in major campaigns to convince the consumer that the addition of the ingredient of a specific manufacturer will serve to achieve this purpose. Thus we find, in different periods over the last years, skin creams containing Vitamin E, skin creams containing Aloe Vera, skin creams containing Jojoba Oil, and even placenta extract, as well as many similar products.

All of these products, however, are based on the same mistaken premise that the youthful appearance of the skin can be regained by providing external nourishment to the skin.

In contradistinction to the above approach, it has now been discovered that the youthful appearance of the skin is a result of healthy nutrients being provided naturally from the circulatory system of the individual.

Thus, instead of trying to artificially apply to the surface of the skin a beneficial active ingredient purported to provide external nourishment and rejuvenation to the skin cells, the present invention provides the novel approach of applying to the surface of the skin a topical composition adapted to aid the body in providing proper circulation to the skin cells, whereby the youthful appearance of the skin is restored, since the skin is once again receiving the same beneficial nourishing circulation which it enjoyed when the body was young. The novel composition and method of the present invention are based on the new concept of bringing blood once again to areas from which it has partially or totally disappeared, and thereby to reestablish the circulatory blood pathway of youth.

The present invention therefore provides a topical composition for rejuvenating skin texture, comprising a first topically applicable component for stimulating the flow of blood in the arteries leading to and the capillaries feeding the muscles adjacent the skin, and a second topically applicable component for stimulating the flow of blood in the capillaries adjacent skin cells.

In preferred embodiments of the present invention, there is provided a topical composition for rejuvenating skin texture, comprising tincture of cayenne pepper as said first active ingredient, in combination with a second active ingredient selected from a tincture of vaccinium myrtillus, gingko biloba, thyme, or a mixture thereof.

The invention also provides a method for rejuvenating skin texture, comprising applying to the skin surface a topical composition comprising a first topically applicable component for stimulating the flow of blood in the arteries leading to and the capillaries feeding the muscles adjacent the skin, and a second topically applicable component for stimulating the flow of blood in the capillaries adjacent skin cells.

In preferred embodiments of the present invention, said method comprises applying to the skin surface a topical composition comprising tincture of cayenne pepper as said first active ingredient, in combination with a second active ingredient selected from a tincture of vaccinium myrtillus, gingko biloba, thyme, or a mixture thereof.

The term "skin surface" as used herein is also intended to include the surface of the scalp; and the term "rejuvenating skin" includes the rejuvenation of the scalp with the result of improved hair growth, as described and exemplified hereinbelow.

Cayenne pepper (capsicum annum) is a well-known condiment used in herbal medicine, and it is even described for use as a linament, since it will quickly bring blood to the surface of the skin. As is known, however, a liniment is a preparation used for sprains, bruises, aches and pains, and thus this prior use did not heretofore suggest to men skilled in the art the presently proposed novel use for this component, since such linaments were not applied to the facial area and heretofore the basic premise upon which the present invention is based, i.e., that rejuvenation of the skin is achieved through renewing the circulation of the blood, was not suggested in the literature.

In preferred embodiments of the present invention, said composition comprises about one part of pure tincture of cayenne pepper as first active ingredient, and two parts of a combination of second active ingredients selected from tinctures of vaccinium nyrtillus, thyme and gingko biloba. To this mixture there are added several drops of an essential aromatic oil, selected from salvia (salvia officinalis, otherwise known as sage), hyssop (hyssopus officinalis), geranium, and marjoram.

This mixture can then be applied in liquid or gel form, or blended in a topically acceptable carrier, such as in a base of calandula or marigold cream.

As will be realized, a variety of topically acceptable carriers can be used for administering the active ingredients of the present invention; however, an especially preferred carrier comprises marigold cream, lanolin oil, or a mixture thereof.

The above ingredients are all natural ingredients, freely available and well-documented in the literature, and known to have no deleterious effects. Thus the composiion of the present invention can be readily prepared and administered.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Example 1

A topical composition was prepared from 2 cc of a tincture of cayenne pepper prescribed at a homeopathic drug store, 2 cc of a tincture of vaccinium myrtillus and 2 cc of thyme. To this mixture there were added 10 drops of H.E. Salvia and 10 drops of H.E. Hyssopus. These active ingredients were added to a carrier of 90% marigold (calandula) cream and 10% lanolin oil.

The resulting product was applied twice daily to the facial skin of several volunteers, and a marked rejuvenating effect in facial texture. A reduction of wrinkles was noted after a few days, while a more youthful appearance of the treated skin was noted already within a few hours. No adverse effects were reported.

Example 2

A further topical composition was prepared from 2cc of a tincture of cayenne pepper, 2 cc of a tincture of gingko biloba, and 2 cc of thyme. To this mixture there were added 10 drops of H.E. Salvia and 10 drops of H.E. marjoram. These active ingredients were added to a carrier of 90% marigold (calandula) cream and 10% lanolin oil.

The resulting product was applied twice daily to the facial skin of several volunteers, and a marked rejuvenating effect in facial texture. A reduction of wrinkles was noted after a few days, while a more youthful appearance of the treated skin was noted already within a few hours. No adverse effects were reported.

Example 3

A further topical composition was prepared from 25 cc of a tincture of cayenne pepper, 25 cc of a tincture of vaccinium martillus, 25 cc of thyme, and 19 cc pure tincture of marigold (calandula). To this mixture there were added 10 drops of H.E. Salvia and 10 drops of H.E. marjoram in a carrier liquid, such as almond oil or wheat germ oil, forming a total composition of 100 cc.

The resulting liquid product was applied twice daily to the scalps of several volunteers, and an improvement in hair growth, also attributable to increased blood circulation in the skin cells and hair roots of the scalp, was noted in different volunteers between a two-month and six-month period. No adverse effects were reported.

The above formulation can be converted to a topical gel by the addition of a gelling agent, such as agar-agar.

Example 4

A topical composition was prepared from 10 cc of a tincture of cayenne pepper obtained at a homeopathic drug store, 10 cc of a tincture of vaccinium myrtillus and 10 cc of thyme. To this mixture there were added 10 drops of H.E. Salvia and 10 drops of geranium. These active ingredients were added to a carrier of 90% marigold (calandula) cream and 10% lanolin oil, to form a total composition of 100 cc.

The resulting product was applied twice daily to the facial skin of several volunteers, and a marked rejuvenating effect in facial texture. A reduction of wrinkles was noted after a few days, while a more youthful appearance of the treated skin was noted already within a few hours. No adverse effects were reported.

Example 5

A further topical composition was prepared from 10 cc of a tincture of cayenne pepper, 10 cc of a tincture of gingko biloba, and 10 cc of thyme. To this mixture there were added 10 drops of H.E. Salvia and 10 drops of H.E. marjoram. These active ingredients were added to a carrier of 90% marigold (calandula) cream and 10% lanolin oil, to form a total composition of 100 cc.

The resulting product was applied twice daily to the facial skin of several volunteers, and a marked rejuvenating effect in facial texture. A reduction of wrinkles was noted after a few days, while a more youthful appearance of the treated skin was noted already within a few hours. No adverse effects were reported.

Example 6

A further topical composition was prepared from 20 cc of a pure tincture of cayenne pepper, 20 cc of a pure tincture of vaccinium martillus, and 20 cc of a pure tincture of thyme, 20 cc of a pure tincture of gingko biloba and 19 cc pure tincture of marigold. To this mixture there were added 10 drops of H.E. Salvia and 10 drops of geranium, to form a total composition of 100 cc.

The resulting liquid product was applied twice daily to the scalps of several volunteers, and an improvement in hair growth, also attributable to increased blood circulation in the skin cells and hair roots of the scalp, was noted in different volunteers between a two-month and six-month period. No adverse effects were reported.

it will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

It will also be realized that the components of the composition of the present invention can be available as dilutions in two or three different concentrations. This permits increasing the dosage gradually, according to the immunological-allergological principles for standardized active factors.

What is claimed is:

1. A topical composition for rejuvenating skin texture, comprising a first active ingredient comprising cayenne pepper for stimulating the flow of blood in the arteries leading to the muscles, and the capillaries feeding the muscles, adjacent the skin; and a second active ingredient selected from the group consisting of vaccinium myrtillus, gingko biloba, thyme, or a mixture thereof, for stimulating the flow of blood in the capillaries adjacent skin cells, said first active ingredient being present in an amount sufficient to stimulate the flow of blood in the arteries leading to the muscles, and the capillaries feeding the muscles, adjacent the skin, and said second active ingredient being present in an amount sufficient to stimulate the flow of blood in the capillaries adjacent skin cells.

2. A topical composition for rejuvenating skin texture as claimed in claim 1, further comprising an essential aromatic oil.

3. A topical composition for rejuvenating skin texture as claimed in claim 2, wherein said essential aromatic oil is selected from the group consisting of hyssop, salvia, geranium and marjoram.

4. A topical composition for rejuvenating skin texture as claimed in claim 1, further comprising a topically acceptable carrier.

5. A topical composition for rejuvenating skin texture as claimed in claim 4, wherein said carrier comprises marigold cream, lanolin oil, or a mixture thereof.

6. A topical composition according to claim 1, further comprising marigold, H.E. Salvia and geranium.

7. A method for rejuvenating skin texture, comprising applying to the skin surface a topical composition comprising a first active ingredient comprising cayenne pepper for stimulating the flow of blood in the arteries leading to the muscles, and the capillaries feeding the muscles, adjacent the skin; and a second active ingredient selected from the group consisting of vaccinium myrtillus, gingko biloba, thyme, or a mixture thereof, for stimulating the flow of blood in the capillaries adjacent skin cells, said first active ingredient being present in an amount sufficient to stimulate the flow of blood in the arteries leading to the muscles, and the capillaries feeding the muscles, adjacent the skin, and said second active ingredient being present in an amount sufficient to stimulate the flow of blood in the capillaries adjacent skin cells.

8. A method according to claim 7 wherein said skin is facial skin.

9. A method according to claim 8 wherein said composition further comprises an essential aromatic oil.

10. A method according to claim 9 wherein said essential aromatic oil is selected from the group consisting off hyssop, salvia, geranium and marjoram.

11. A method according to claim 8 wherein said composition further comprises a topically acceptable carrier.

12. A method according to claim 11 wherein said carrier comprises marigold cream, lanolin oil, or a mixture thereof.

13. A method according to claim 8 wherein said first active ingredient comprises cayenne pepper, and wherein said second active ingredient comprises a mixture of vaccinium martillus, gingko biloba and thyme.

14. A method according to claim 8 wherein said composition further comprises marigold, H.E. Salvia and geranium.

* * * * *